(12) United States Patent
Bottom

(10) Patent No.: US 7,418,964 B2
(45) Date of Patent: Sep. 2, 2008

(54) ANESTHETIC AGENT CASSETTE WITH OVERLAID ANALOG/DIGITAL SIGNAL INTERFACES

(75) Inventor: Douglas Kirk Bottom, Watertown, WI (US)

(73) Assignee: GE Medical Systems Information Technologies, Milwaukee, WI (US)

( * ) Notice: Subject to any disclaimer, the term of this patent is extended or adjusted under 35 U.S.C. 154(b) by 634 days.

(21) Appl. No.: 11/103,109

(22) Filed: Apr. 11, 2005

(65) Prior Publication Data

US 2006/0225736 A1 Oct. 12, 2006

(51) Int. Cl.
*A61M 15/00* (2006.01)

(52) U.S. Cl. .............................. 128/203.15; 128/203.12; 141/95

(58) Field of Classification Search .................... 141/94, 141/95, 192, 198; 128/203.12, 203.15, 204.18, 128/204.22

See application file for complete search history.

(56) References Cited

U.S. PATENT DOCUMENTS

| | | | |
|---|---|---|---|
| 5,806,513 A * | 9/1998 | Tham et al. ............ | 128/204.22 |
| 6,216,690 B1 * | 4/2001 | Keitel et al. ............ | 128/203.12 |
| 6,672,306 B2 * | 1/2004 | Loser et al. ............ | 128/203.12 |
| 6,719,019 B2 * | 4/2004 | Cao et al. ................... | 141/100 |
| 6,745,800 B1 | 6/2004 | Sansom | |

OTHER PUBLICATIONS

S/5 ADU Carestation®, An integrated solution for quality care; GE Healthcare; AN3203-D Sep. 2004.
S/5 ADU Aladin™ Cassette, Datex-Ohmeda.

* cited by examiner

*Primary Examiner*—Timothy L Maust
(74) *Attorney, Agent, or Firm*—Andrus, Sceales, Starke & Sawall, LLP

(57) ABSTRACT

An anesthetic agent cassette is provided for selectively communicating with an anesthesia machine using either analog or digital communication techniques. The anesthetic agent cassette includes an input contact that receives an input signal from an anesthesia machine. Based upon the input signal, the control circuit in the anesthetic agent cassette determines whether the anesthetic agent cassette is coupled to an anesthesia machine that utilizes either digital communication or analog communication. The anesthetic agent cassette includes an output circuit that selectively connects either a digital output line or an analog output line to a single output contact.

14 Claims, 2 Drawing Sheets

ANESTHETIC AGENT CASSETTE WITH OVERLAID ANALOG/DIGITAL SIGNAL INTERFACES

BACKGROUND OF THE INVENTION

The present invention generally relates to an electrical signal interface between an anesthesia machine and an anesthetic agent cassette. More specifically, the present invention relates to an electrical signal interface contained within a removable anesthetic agent cassette that allows the single, common anesthetic agent cassette to communicate using analog communication with a legacy, analog anesthesia machine and digital communication with a digital anesthesia machine.

During the supply of anesthesia, the gaseous anesthetic agent inhaled by the patient is formed of oxygen, nitrogen, nitrous oxide and an inhalation anesthetic agent. Inhalation anesthetics are typically in liquid form at administration temperatures, and an anesthetic vaporizer is needed to gasify the liquid. Anesthetic vaporizers have a drug reservoir for storing the supply of agent to be vaporized. The vaporized anesthetic is administered for the patient to inhale by means of a carrier gas flow.

Presently, many types of anesthesia machines receive an anesthetic vaporizer that can be configured in the shape of a cassette such that different cassettes can be easily removed and replaced from the anesthesia machine depending upon the type of anesthetic agent to be delivered. One example of such a cassette is the Aladin™ cassette available from Datex-Ohmeda, Inc. The anesthetic agent cassette includes electronic circuitry that monitors the liquid level of the anesthetic agent remaining within the reservoir. The electronic circuitry contained within the anesthetic agent cassette communicates back to the control circuitry of the anesthesia machine such that the anesthesia machine can signal to an operator when the level of anesthetic agent within the reservoir of the agent cassette falls below an acceptable value.

Presently, many of the anesthesia machines in use, such as the S/5 ADU Carestation® also available from Datex-Ohmeda, utilize analog communications between the electronic circuitry within the anesthetic agent cassette and the anesthesia machine. However, the analog communication technique utilized between the anesthesia machine and the agent cassette is being replaced by digital communications that allows additional information to be relayed between the anesthesia machine and the agent cassette.

Anesthetic agent cassettes being developed for use with newer anesthetic machines include enhanced measuring and reporting abilities that communicate using digital signals. In a hospital or critical care environment that utilizes the two types of anesthesia machines that communicate by analog or digital signals, the facility will be required to purchase and own two different types of anesthetic agent cassettes that can be utilized on either an analog anesthesia machine or a digital anesthesia machine. Therefore, a need exists for an anesthetic agent cassette that can be utilized with both an anesthesia machine using digital communications and an anesthesia machine using analog communications.

SUMMARY OF THE INVENTION

The present invention is an anesthetic agent cassette for use with anesthesia machines that communicate using either analog communication or digital communication. The single type of anesthetic agent cassette can thus be utilized with two different types of anesthesia machines, thereby reducing the number of anesthetic agent cassettes required.

The anesthetic agent cassette includes an input contact positioned to selectively receive an input signal from the anesthesia machine to which it is connected. The input contact is coupled to a control circuit contained within the anesthetic agent cassette. When the anesthetic agent cassette is coupled to an anesthesia machine that communicates using digital communications, the anesthesia machine provides an input signal at the input contact, which is thus received by the control circuit. If the anesthetic agent cassette is coupled to an anesthesia machine that communicates using analog communications, the anesthesia machine does not generate an input signal and thus no input signal is received by the anesthetic agent cassette.

The anesthetic agent cassette includes a bias device coupled to the input contact such that when no input signal is present, the bias device creates a constant, low value at the input to the control circuit. The control circuit is able to determine the type of anesthesia machine connected to the anesthetic agent cassette based upon whether the input is either a constant, low value or a high or alternating value as represented on the input signal.

The anesthetic agent cassette includes an output circuit that feeds a single output contact. The output circuit includes a digital output line and an analog output line that are each connected to the control circuit. The analog output line is connected to the output contact by a first selection switch, while the digital output line is connected to the same output contact through a second selection switch. Both the first and second selection switches are operable between an open and a closed position and are each coupled to a switch control line. Based upon the type of anesthesia machine detected by the control circuit, the control circuit generates a selection signal along the switch control line, which controls the opening and closing of the first and second selection switches.

If the control circuit detects an anesthesia machine that communicates using analog communication, the control circuit closes the first selection switch and opens the second selection switch such that only the analog output line is coupled to the output contact. Likewise, if the control circuit determines that the anesthesia machine communicates using digital communication, the control circuit closes the second selection switch and opens the first selection switch such that only the digital output line is connected to the output contact. Thus, the single anesthetic agent cassette can be utilized with anesthesia machines that communicate using either digital communication or analog communication.

BRIEF DESCRIPTION OF THE DRAWINGS

The drawings illustrate the best mode present contemplated in carrying out the invention. In the drawings.

DETAILED DESCRIPTION OF THE PREFERRED EMBODIMENT

Figure 1:
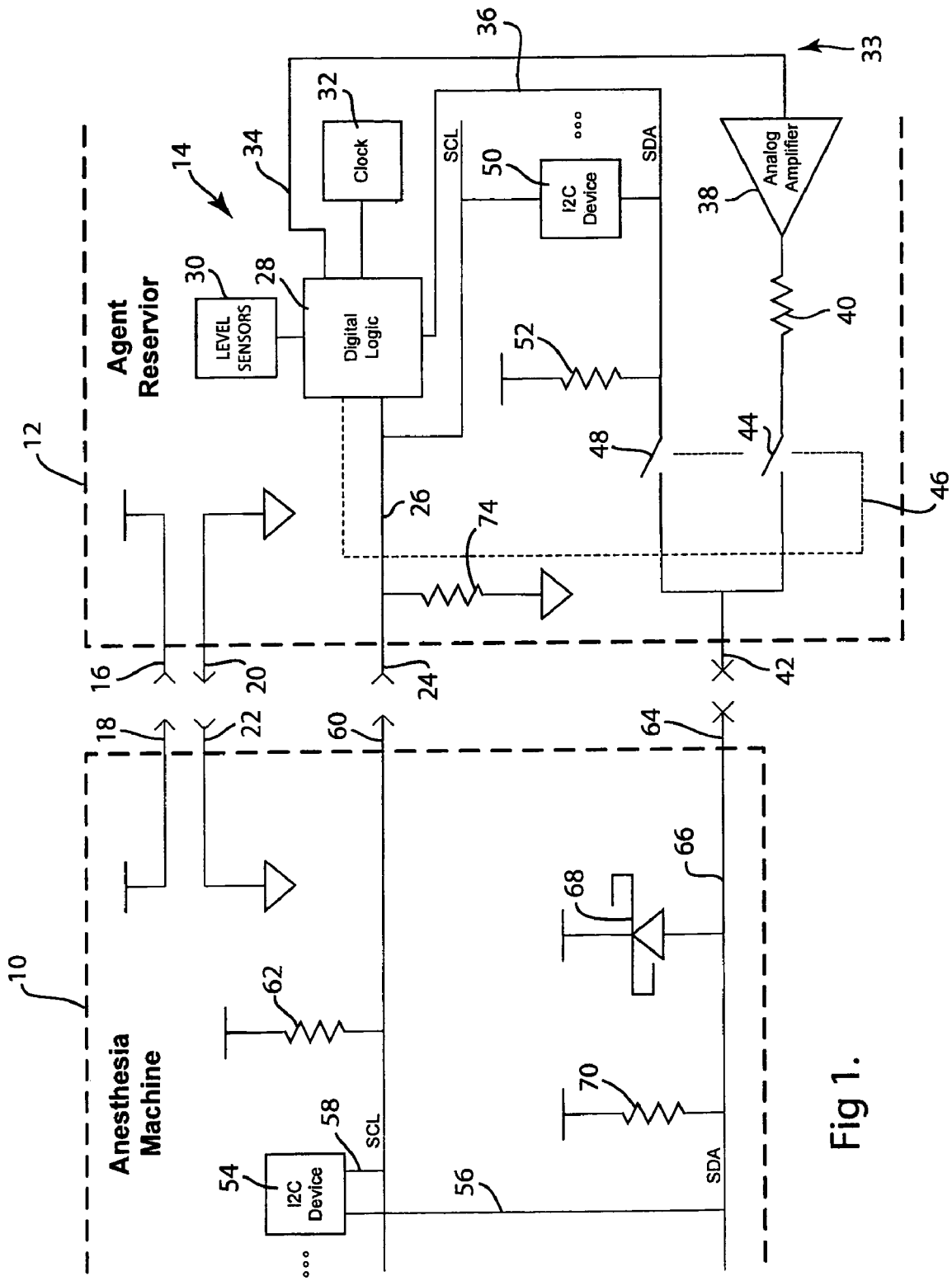
FIG. 1 is a schematic illustration of the interface between the anesthetic agent cassette of the present invention and an anesthesia machine that communicates using digital communication.

Referring first to FIG. 1, thereshown is the communication interface between a digital anesthesia machine 10 and an anesthetic agent cassette 12 of the present invention. The digital anesthesia machine 10 communicates with the anesthetic agent cassette 12 using digital communication techniques. An example of such a digital anesthesia machine is the AISYS™ model available from Datex-Ohmeda, Inc., Madison, Wis. The anesthetic agent cassette 12 is similar to the Aladin™ model also available from Datex-Ohmeda, Inc. Unlike the previously available agent cassettes, the anesthetic agent cassette 12 of the present invention allows communication between both the digital anesthesia machine 10 and a legacy, analog anesthesia machine as will be described in greater detail below.

The anesthetic agent cassette 12 is removably connectable to the anesthesia machine 10 such that a supply of anesthetic agent can be delivered to a patient by the anesthesia machine 10. The anesthetic agent cassette 12 is removable from the anesthesia machine 10 such that different types of anesthetic agents can be supplied for use by the anesthesia machine by simply removing the cassette 12 and replacing the cassette with a different cassette specifically designed for a different type of anesthetic agent. The anesthetic agent cassette 12 includes an agent reservoir that receives the liquid supply of the anesthetic agent, a filling port (not shown) and electronic circuitry 14.

As illustrated in FIG. 1, the anesthetic agent cassette 12 includes four separate contact pins schematically illustrated as extending from the anesthetic agent cassette 12. The first contact is a power contact 16 that is positioned to receive and engage a similar power contact 18 of the digital anesthesia machine 10. The power contact 16 receives the operating power for the electronic circuitry 14 from the anesthesia machine 10. A power return contact 20 engages a similar power return contact 22 formed on the anesthesia machine 10 to complete the electrical connection.

The anesthetic agent cassette 12 further includes an input contact 24 that is connected by input line 26 to a control circuit 28 of the electronic circuitry 14. The control circuit 28 receives input signals from a plurality of level sensors 30 and a timing signal from clock 32. In the preferred embodiment of the invention, the agent cassette 12 includes five level sensors 30 that are used to detect the amount of liquid present in the reservoir of the agent cassette 12. In each of these sensors is a photo reflective sensor that is used in on/off fashion to determine the level of liquid agent within the anesthetic agent cassette 12. The sensed information from the level sensors 30 is input into the control circuit 28 such that the control circuit 28 can determine the amount of anesthetic agent contained within the agent cassette 12.

Based upon the level of anesthetic agent sensed by the level sensors 30, the control circuit 28 generates an output signal to an output circuit 33. Specifically, the control circuit generates an analog signal along analog output line 34 of the output circuit 33 and a digital signal representing the liquid level along the digital output line 36 of the output circuit 33. As illustrated in FIG. 1, the analog output line 34 is fed to an analog amplifier 38, whose output is coupled to an isolation resistor 40. The isolation resistor 40 is connected to an output contact 42 of the anesthetic agent cassette 12 through a first selection switch 44. The first selection switch 44 of the output circuit 33 is a normally open switch, the position of which is controlled by a switch control line 46. The switch control line 46 receives a selection signal from the control circuit 28.

The digital output line 36 from the control circuit 28 is also connected to the same output contact 42 through a second selection switch 48 of the output circuit 33. The second selection switch 48 is also connected to the switch control line 46 such that a selection signal generated by the control circuit 28 can control the open and closed position of the second selection switch 48. In addition to the digital output from the control circuit 28, the digital output line 36 is also connected to one or more electronic devices 50. In the embodiment of the invention illustrated in FIG. 1, the electronic devices 50 are I²C devices. As used in this description and as is well known to one of ordinary skill in the art, an I²C device is a device that communicates utilizing a Philips I²C bus. The I²C bus specification is available from Philips and is a well known communication specification whose specifics will not be discussed in greater detail. As an example, the I²C device could be a temperature sensing device, a pressure sensing device, an error reporting device or any other device that communicates over a digital bus using the I²C bus specification. Each of the electronic devices 50 includes both a serial data and address (SDA) line and a serial clock line (SCL) in accordance with I²C bus specification. A pull-up resistor 52 is coupled to the digital output line 36 to comply with the I²C specification.

As illustrated in FIG. 1, the digital anesthesia machine 10 includes a plurality of electronic devices 54 that also communicate internally using the I²C bus specification. Each of the electronic devices 54 includes both a serial data and address (SDA) line 56 and a serial clock line (SCL) 58 in accordance with I²C bus specification. The SCL line 58 of each of the operating devices 54 is connected to an output contact 60 of the digital anesthesia machine 10. A pull-up resistor 62 is connected to the SCL line 58 in accordance with I²C bus specification. As illustrated in FIG. 1, the output contact 60 of the digital anesthesia machine 10 is aligned to engage an input contact 24 of the anesthetic agent cassette 12. Since the anesthesia machine 10 is a digital device, the signal level on the SCL line is either a high or alternating signal defined by the clock pulse signal.

When the anesthetic agent cassette 12 is connected to the digital anesthesia machine 10, the input contact 24 receives an input signal on input line 26. Specifically, the input signal is the high or alternating clock signal present on the SCL line 58 which is transferred to the anesthetic agent cassette 12 by the output contact 60. When the control circuit 28 senses the present of the high or alternating input signal along input line 26, the control circuit 28 generates a selection signal to the output circuit 33 that closes the second selection switch 48 and opens the first selection switch 44. When the second selection switch 48 is closed and the first selection switch 44 opens, the digital output line 36 is connected to the output contact 42. Thus, when the control circuit 28 senses the high or alternating input signal, the anesthetic agent cassette 12 generates a digital output signal at output contact 42.

The digital output signal is received by an input contact 64 of the digital anesthesia machine 10. The input contact 64 is connected to a digital communication line 66, which is also coupled to the SDA line 56 of each of the operating devices 54. A diode 68 provides over voltage protection and a pull up resistor 70 is required for the I²C bus protocol.

As can be understood in FIG. 1, the anesthetic agent cassette 12 can be connected to the digital anesthesia machine 10 such that the anesthetic agent cassette 12 communicates the required information, such as anesthetic agent level, temperature, and pressure using a digital communication interface between the single output contact 42 and the input contact 64. The control circuit 28 controls the position of the first and second selection switches 44, 48 such that the digital output line 36 is connected to the output contact 42 when the digital logic circuit 28 senses the high or alternating input signal at the input contact 24.

Figure 2:
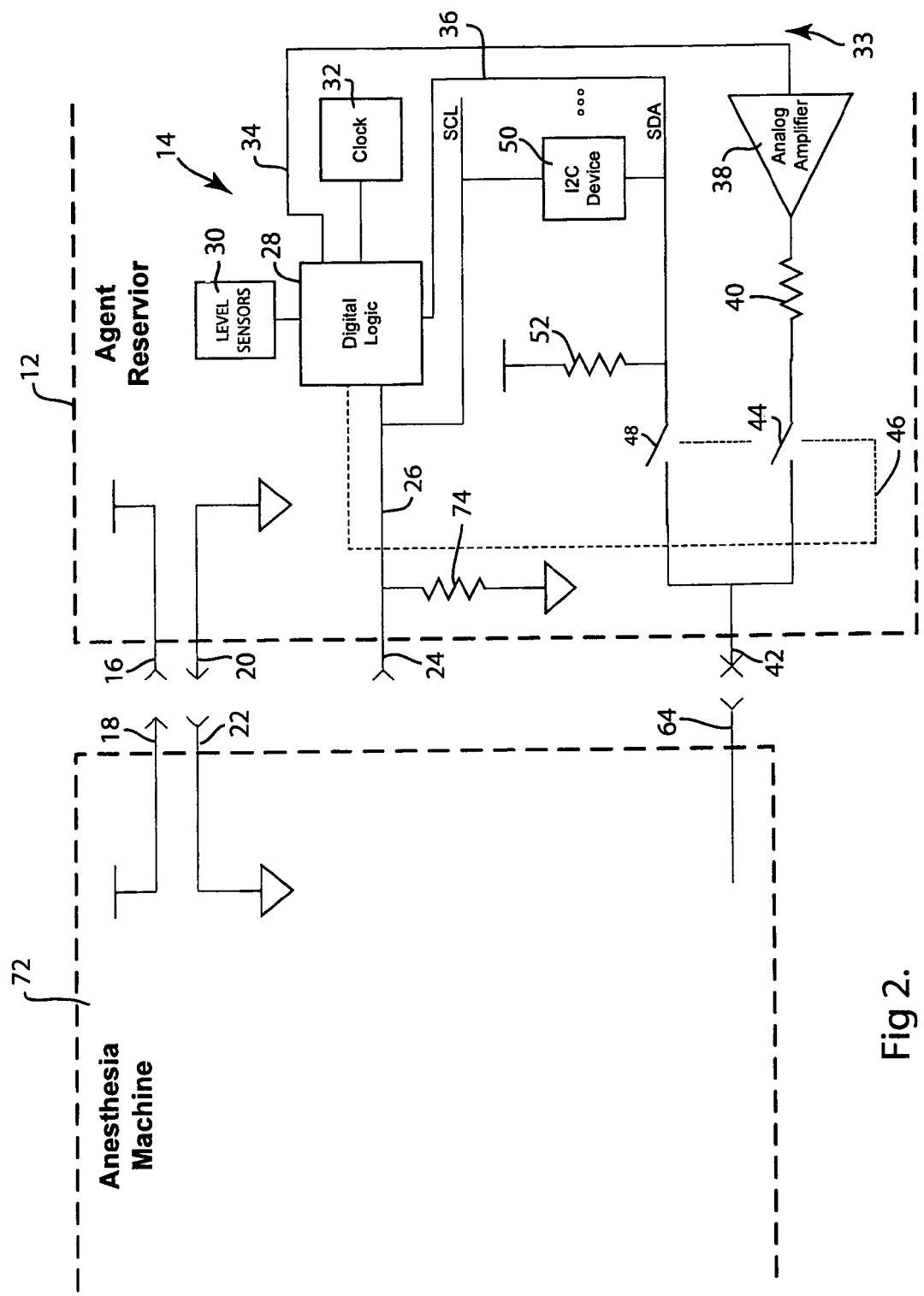
FIG. 2 is a schematic illustration of the interface between the anesthetic agent cassette of the present invention and an anesthesia machine that communications using analog communication.

Referring now to FIG. 2, thereshown in the interconnection between the same anesthetic agent cassette 12 and an analog anesthesia machine 72. The analog anesthesia machine 72 includes both the power contact 18 and power return contact 22 that engage the power contact 16 and power return contact 20, respectively, of the anesthetic agent cassette 12. Unlike the digital anesthesia machine 10 shown in FIG. 1, the analog anesthesia machine 72 does not include an output contact 60 (FIG. 1) that engages the input contact 24 of the anesthetic agent cassette 12. Since the input contact 24 does not receive the clock signal from the analog anesthesia machine 72, the high or alternating input signal is not present on input line 26. Instead, a pull-down resistor 74 pulls the input line 26 to a constant, low level, which is sensed by the control circuit 28. When the control circuit 28 senses the constant low level on input line 26, the control circuit 28 determines that the anesthetic agent cassette 12 is connected to an analog anesthesia machine 72.

When the control circuit 28 determines that the anesthesia machine 72 is an analog anesthesia machine, the control circuit generates a selection signal to the output circuit 33 along the switch control line 46. The selection signal causes the second selection switch 48 to open and the first selection switch 44 to close. When the first selection switch 44 is closed and the second selection switch 48 is open, the analog output line 34 is connected to the output contact 42. The output contact 42 is received by the input contact 64 of the anesthesia machine 72 such that analog signals corresponding to the liquid level sensed by the liquid level sensors 30 can be received by the control circuit of the analog anesthesia machine 72. The control circuit 28 operates such that only one of the first selection switch 44 and the second selection switch 48 are closed at any time. Thus, either an analog signal or a digital signal is present at the output contact 42, not both.

As can be understood by the above description, the single anesthetic agent cassette 12 can be utilized with both a digital anesthesia machine 10 and a analog anesthesia machine 72. Thus, a healthcare facility utilizing both digital and analog anesthesia machines does not need to inventory different anesthetic agent cassettes for each type of anesthesia machine. Instead, the facility can utilize the single type of anesthetic agent cassette 12 for both types of anesthesia machines.

What is claimed is:

1. An anesthetic agent cassette for use with an anesthesia machine, the agent cassette comprising:
    an input contact positioned to selectively receive an input signal from the anesthesia machine;
    a control circuit coupled to the input contact, wherein the control circuit is operable to generate a selection signal based upon the input signal; and
    an output circuit in communication with the control circuit to receive the selection signal, the output circuit including an analog output line coupled to an output contact by a first selection switch and a digital output line coupled to the output contact by a second selection switch, wherein the position of the first and second selection switches is controlled by the selection signal.

2. The anesthetic agent cassette of claim 1 wherein the control circuit senses the presence of the input signal at the input contact and closes the second selection switch to couple the digital output line to the output contact only upon detection of the input signal.

3. The anesthetic agent cassette of claim 2 wherein the input signal from the anesthetic machine is an alternating signal.

4. The anesthetic agent cassette of claim 1 wherein only one of the first selection switch and the second selection switch are closed at the same time.

5. The anesthetic agent cassette of claim 1 wherein the control circuit closes the first selection switch to couple the analog output line to the output contact when the input signal from the anesthetic machine is not present at the input contact.

6. The anesthetic agent cassette of claim 1 wherein the digital output line is coupled to at least one electronic device.

7. The anesthetic agent cassette of claim 6 wherein the electronic device is a liquid level sensor.

8. The anesthetic agent cassette of claim 1 further comprising a bias resistor connected to the input contact, wherein the bias resistor creates a bias level received by the control circuit in the absence of the input signal from the anesthetic machine.

9. An anesthetic agent cassette for use with both a first anesthesia machine that communicates with the anesthetic agent cassette using digital communication and a second anesthesia machine that communicates with the anesthesia agent cassette using analog communication, the anesthetic agent cassette comprising:
    an input contact positioned to selectively receive an input signal from the first anesthesia machine;
    a control circuit coupled to the input contact, the control circuit being operable to generate a selection signal based upon the presence of the input signal at the input contact; and
    an output circuit in communication with the control circuit to receive the selection signal, the output circuit including an analog output line coupled to an output contact by a first selection switch and a digital output line coupled to the output contact by a second selection switch, wherein the position of the first and second selection switches is controlled by the selection signal.

10. The anesthetic agent cassette of claim 9 wherein the control circuit closes the second selection switch to couple the digital output line to the output contact upon detection of the input signal.

11. The anesthetic agent cassette of claim 10 wherein the input signal from the first anesthesia machine is an alternating signal.

12. The anesthetic agent cassette of claim 9 wherein only one of the first selection switch and the second selection switch are closed at the same time.

13. The anesthetic agent cassette of claim 9 further comprising a bias resistor connected to the input contact, wherein the biased resistor creates a bias level received by the control circuit when the anesthetic agent cassette is coupled to the second anesthesia machine.

14. The anesthetic agent cassette of claim 12 wherein the control circuit closes the first selection switch to couple the analog output line to the output contact upon detection of the bias level by the control circuit.

* * * * *